(12) United States Patent
Gabriel et al.

(10) Patent No.: US 6,265,610 B1
(45) Date of Patent: Jul. 24, 2001

(54) CONTRAST MEDIA FOR ANGIOGRAPHY

(75) Inventors: Don A. Gabriel, Carrboro; Laura J. Melton, Durham, both of NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/480,429

(22) Filed: Jan. 11, 2000

Related U.S. Application Data

(60) Provisional application No. 60/115,586, filed on Jan. 12, 1999.

(51) Int. Cl.[7] .................... C07C 233/05; C07D 207/04; C07D 211/16; A61K 49/04
(52) U.S. Cl. .................. 564/153; 424/9.452; 514/330; 514/423; 514/424; 514/616; 546/226; 548/540
(58) Field of Search .......................... 546/226; 548/540; 564/153; 424/9.452; 514/616, 330, 423, 424

(56) References Cited

U.S. PATENT DOCUMENTS

| | | | |
|---|---|---|---|
| 3,953,501 | 4/1976 | Klieger et al. | 260/518 A |
| 4,005,188 | 1/1977 | Tilly et al. | 424/5 |
| 4,014,986 | 3/1977 | Tilly et al. | 424/5 |
| 4,065,553 | 12/1977 | Tilly et al. | 424/5 |
| 4,065,554 | 12/1977 | Tilly et al. | 424/5 |
| 4,094,966 | 6/1978 | Tilly et al. | 424/5 |
| 4,225,577 | 9/1980 | Tilly et al. | 424/5 |
| 4,264,572 | 4/1981 | Klieger et al. | 424/5 |
| 4,474,747 | 10/1984 | Dimo et al. | 424/5 |
| 5,075,501 | 12/1991 | Borland et al. | 564/297 |
| 5,324,503 | 6/1994 | Lin et al. | 424/5 |
| 5,550,287 | 8/1996 | Cannata et al. | 564/153 |
| 5,567,410 | 10/1996 | Torchilin et al. | 424/9.4 |
| 5,571,941 | 11/1996 | Villa et al. | 564/153 |
| 5,616,798 | 4/1997 | Dugast-Zrihen et al. | 564/153 |
| 5,618,977 | 4/1997 | Dugast-Zrihen et al. | 564/153 |
| 5,628,980 | 5/1997 | Ranganathan et al. | 424/5 |

OTHER PUBLICATIONS

P. Dawson; *Embolic Problems in Angiography*, Seminary in Hematology, 28(4)Suppl 7:31–37 (1991).

Eaton et al.; *A Study of the Anticoagulation Mechanisms of X–Ray Contrast Media*, Investigative Radiology, 29(Suppl 2):S201–S202 (1994).

Hwang et al.; *The Potential Risk of Thrombosis During Coronary Angiography Using Nonionic Contrast Media*, Catheterization and Cardiovascular Diagnosis, 16:209–213 (1989).

Don A. Gabriel; *Effects of Contrast Agents on Fibrin Structure and Platelet Surface Charge*, Research Review, 3(Supple B):31B–39B (1991).

Grollman, Jr., et al.; *Thromboembolic Complications in Coronary Angiography Associated With the Use of Nonionic Contrast Medium*, Catheterization and Cardiovascular Diagnosis, 14:159–164 (1988).

Kikumoto et al.; *Thrombin Inhibitors. 2. Amide Derivatives of $N^\alpha$–Substituted L–Arginine*, J. of Med. Chem., 23(8):830–836 (1980).

Eloy et al.; *Contrast Media for Angiography: Physiochemical Properties, Pharmacokinetics and Biocompatibility*, Clinical Materials, 7:89–197 (1991).

Sturzebecher et al., *Cyclic Amides of N Alpha–Arylsulfonylaminoacylated 4–Amidinophenylalanine—Tight Binding Inhibitors of Thrombin*, Thromb Res, 29(6):636 (1983).

PCT International Search Report PCT/US00/00755, dated May 25, 2000.

*Primary Examiner*—Shailendra Kumar
(74) *Attorney, Agent, or Firm*—Myers Bigel Sibley & Sajovec

(57) ABSTRACT

The present invention provides basic ionic contrast agents that have anticoagulant activity. The contrast media incorporate a lysine or arginine group or derivative, and have a free amino or guanidino group. Methods of using the contrast media are also disclosed.

21 Claims, No Drawings

CONTRAST MEDIA FOR ANGIOGRAPHY

This application claims priority from provisional application Serial No. 60/115,586, filed Jan. 12, 1999, the disclosure of which is incorporated by reference herein in its entirety.

FIELD OF THE INVENTION

The present invention concerns compounds useful as contrast media for angiography, formulations thereof, and methods of using the same. The present invention is particularly concerned with contrast media that have anticoagulant properties.

BACKGROUND OF THE INVENTION

The occurrence of thrombosis during angiographic procedures is problematic. The anticoagulant properties of the currently available commercial contrast media are questionable. The nonionic contrast media are being investigated for their potential role in a thrombotic event during angiography. The ionic contrast media are thought to have some anticoagulant properties, however, they are less tolerated physiologically by the patient compared to nonionic contrast media. Accordingly, the provision of a contrast media with both anticoagulant properties and good physiological properties would be extremely valuable.

U.S. Pat. No. 3,953,501 to Klieger describes compounds of the formula:

$$RCONH-\text{[aryl with CONR}_1R_2, I, I, I]-C(R_3)-N-CO-Y$$

U.S. Pat. No. 4,264,572 to Klieger et al. describes X-Ray contrast media having the following general formula:

$$R_1-CO-N(R_2)-\text{[aryl]}-C(O)-N(R_3)-(CH_2)_n-N(R_4)-\text{[aryl]}-COOH$$
with CONHR$_5$ substituent and Z=COOH analog P. Dawson, Embolic Problems in Angiography, *Seminars in Hematology* 28, 31–37 (1991), states that anticoagulant activity can not be provided in a non-ionic contrast agent without a general increase in toxicity of that agent.

SUMMARY OF THE INVENTION

The present invention provides basic ionic contrast agents that have anticoagulant activity.

A first aspect of the present invention is a compound of Formula I:

Formula I $$R_1-CO-N(R_2)-\text{Ar}(CONR_5R_6, I, I)-C(O)-N(R_3)-(CH_2)_n-N(R_4)-\text{Ar}(CO-Z, I, I)-C(O)-N(H)-CH((CH_2)_o R_{11})-C(O)-N(R_9)(R_{10})$$

wherein:

R1 is selected from the group consisting of alkyl and alkyl substituted with hydroxy or alkoxy;

R2, R3 and R4 are each independently selected from the group consisting of hydrogen and alkyl;

R5 and R6 are each independently selected from the group consisting of hydrogen, alkyl and hydroxyalky, n is from 1 to 3;

Z is —A—NHCH3, or when R1 is hydroxy or alkoxy substituted alkyl and/or when R3 is loweralkyl, Z can also be hydroxy-C2–5-alkylamino;

A is:

$$-N(R_7)-(CH_2)_m-CH(R_8)-CO-$$

wherein

R7 is H or alkyl;

R8 is H, alkyl, or alkyl substituted by hydroxy or alkoxy;

or together R7 and R8 form a propylene or hydroxypropylene ring;

m is 0 or 1;

R9 and R10 are each independently H or alkyl; or R9 and R10 together form C4–C8 (preferably C4) alkylene which is unsubstituted or substituted from one to three times with alkyl (e.g., methyl) or hydroxy;

R11 is amino or guanidino;

o is from two to six, preferably 3 or 4;

or a physiologically acceptable salt thereof.

A second aspect of the present invention is compounds Formula II:

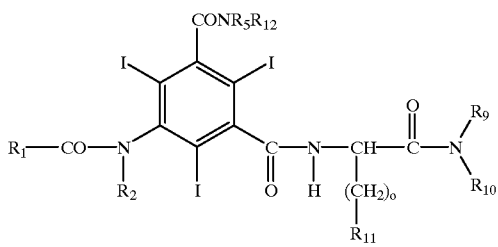

Formula II wherein:
R1 is selected from the group consisting of alkyl and alkyl substituted with hydroxy or alkoxy;
R2 is selected from the group consisting of hydrogen and alkyl;
R5 and R12 are each independently selected from the group consisting of hydrogen, alkyl and hydroxyalky,
R9 and R10 are each independently H or alkyl; or R9 and R10 together form C4–C8 (preferably C5) alkylene which is unsubstituted or substituted from one to three times with alkyl (e.g., methyl) or hydroxy;
R11 is amino or guanidino;
o is from two to six, preferably 3 or 4
or a physiologically acceptable salt thereof.

A third aspect of the present invention is a contrast media comprising an amount of a compound of Formula I or II above effective as a contrast medium in combination with a pharmaceutically acceptable carrier.

A fourth aspect of the present invention is the use of a compound of Formula I or II above for the preparation of a contrast media.

A fifth aspect of the present invention is a method of visualizing an internal organ or structure of a patient which comprises administering to the patient an amount of a compound of Formula I or II above effective as a contrast medium, and then exposing said organ or structure to a diagnostic imaging treatment. The structure to be imaged can be a platelet or fibrin thrombus.

The present invention is explained in greater detail in the specification set forth below.

DETAILED DESCRIPTION OF THE PREFERRED EMBODIMENTS

Organs or structures that may be imaged by the contrast media of the present invention include blood vessels, a thrombus within a vessel, heart, brain, kidney, liver, lungs, spleen, etc. as well as portions thereof. Thus the entirety of an organ or structure need not be imaged, but only the portion thereof of diagnostic interest.

Diagnostic imaging treatments used to carry out the method of the present invention may be of any type, including magnetic resonance imaging and CT, but typically are X-ray diagnostic imaging treatments.

Alkyl as used herein is C1–4 loweralkyl; alkoxy as used herein is C1–C4 lower alkoxy, and more preferably C1–C2 lower alkoxy.

The lower alkyl residue R1, which where appropriate can be substituted singly or multiply, may contain from 1 to 4 carbon atoms, preferably 1 to 2 carbon atoms, in the alkyl residue. Suitable substituents include hydroxy, preferably 1–2 groups, or alkoxy of 1–2 carbon atoms, preferably one group. Preferred lower alkyl residues R1 have 1–2 carbon atoms and may be substituted by hydroxy or alkoxy, such as, e.g., methyl, ethyl, methoxymethyl, hydroxymethyl and the like.

Suitable lower alkyl residues for R2, R3 and R4 have 1–4 carbon atoms, preferably 1–2 carbon atoms, for instance methyl, ethyl, propyl, isopropyl and the like.

Suitable lower alkyl residues for R5 have 1–4 carbon atoms and especially have 1–2 carbon atoms, for instance, methyl or ethyl. This alkyl residue may optionally be substituted by hydroxy, preferably 1–2 groups; n preferably has a value of 1.

When Z is straight-chain or branched hydroxy lower alkylamino, the alkyl residue may contain 2–5 carbon atoms, and, e.g., 1–3 hydroxy substituents. If Z is a straight chain group, the alkyl residue preferably contains 2–5 carbon atoms; if Z is branched, the alkyl residue preferably contains 3–5 carbon atoms. The hydroxy groups in Z may be present as primary or secondary hydroxy groups. Suitable Z residues include, e.g., 2-hydroxypropylamino, 3-hydroxypropylamino, 2-hydroxy-1, 1-dimethylethylamino, 3-hydroxy-1, 1-dimethylpropylamino and, preferably, 2-hydroxyethylamino.

Suitable bridging amino acid residues A include those derived from an amino carboxylic acid of arbitrary configuration. Included are those residues which are equivalents of, e.g., the preferred amino acid residue of the formula

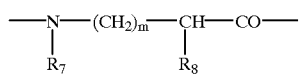

wherein m is 0 or 1, R7 is hydrogen or lower alkyl of 1–4 carbon atoms, preferably 1–2 carbon atoms, R8 is hydrogen or lower alkyl of 1–4 carbon atoms which also may be straight chain or branched and which may be substituted by hydroxy, preferably 1–2 groups or lower alkoxy of 1–2 carbon atoms, preferably 1–2 groups, and wherein R7 and R8 together may form a propylene or hydroxypropylene group. Examples of suitable aminocarboxylic acids include glycine, alanine, valine, serine, O-methylserine, proline, hydroxyproline, leucine, isoleucine, sarcosine, beta-alanine and the like. Especially preferred are alpha-aminocarboxylic acids in which R7 is hydrogen or methyl and R8 is hydrogen or lower alkyl of 1–2 carbon atoms which may be hydroxy- or methoxy-substituted.

Compounds of Formula I are prepared as described in Examples 1–5 below, or variations thereof that will be apparent to those skilled in the art. Examples of such compounds include the following:

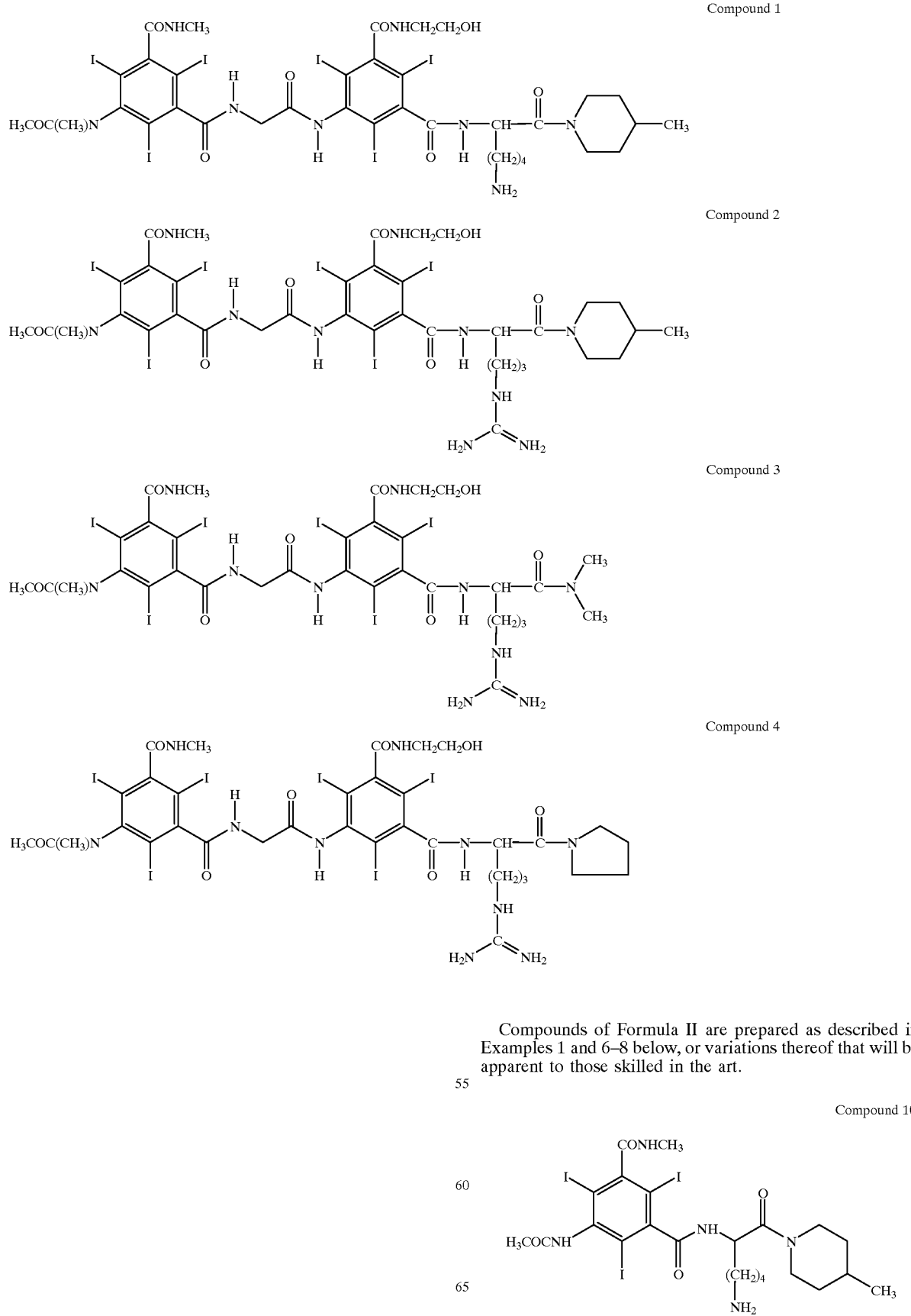
Compounds of Formula II are prepared as described in Examples 1 and 6–8 below, or variations thereof that will be apparent to those skilled in the art.

-continued
Compound 11
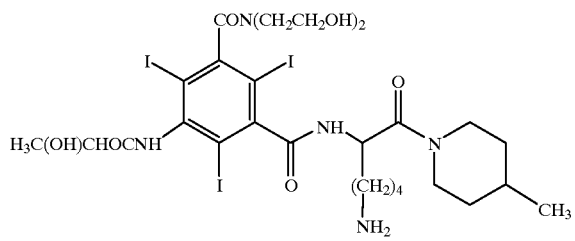
Compound 12
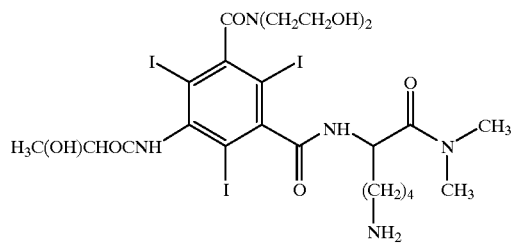
Compound 13
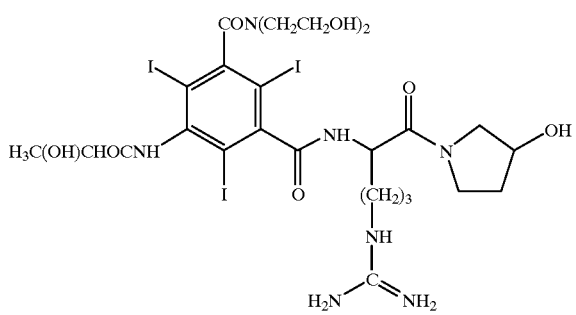
Additional examples of compounds of the invention include the following:
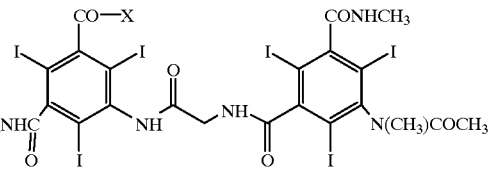
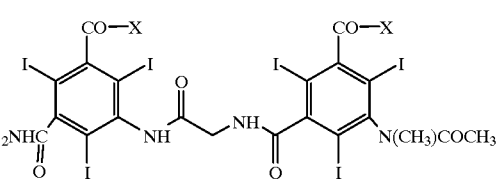
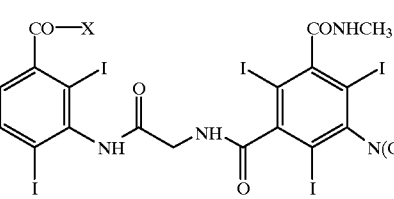
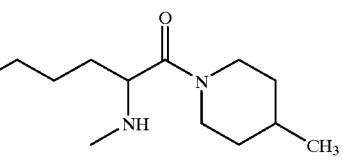
Additional examples of compounds of the invention include the following:
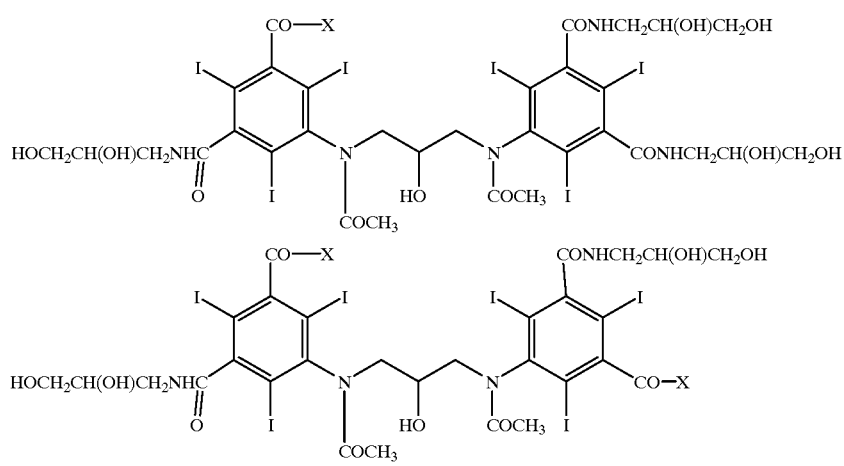

where X is as defined above.

Additional examples of compounds of the invention include the following, were R groups are as defined in the Table below:

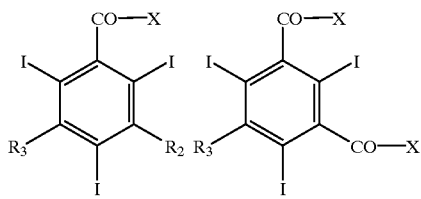

where X is as defined above.

| R$_2$ | R$_3$ |
|---|---|
| 1 CONHCH(CH$_2$OH)$_2$ | NHCOCH(OH)CH$_3$ |
| 2 CONHCH$_2$CH(OH)CH$_2$OH | N(COCH$_3$)CH$_2$CH(OH)CH$_2$OH |
| 3 CONHCH$_2$CH(OH)CH$_2$OH | N(COCH$_2$OH)CH$_2$CH(OH)CH$_2$OH |
| 4 CONHCH$_2$CH$_2$OH | N(COCH$_3$)CH$_2$CH(OH)CH$_2$OH |
| 5 CON(CH$_3$)CH$_2$CHOHCH$_2$OH | NHCOCH$_2$OCH$_3$ |

Still additional examples of compounds of the present invention include the following:

Base (Prior Art) Compound[1]:

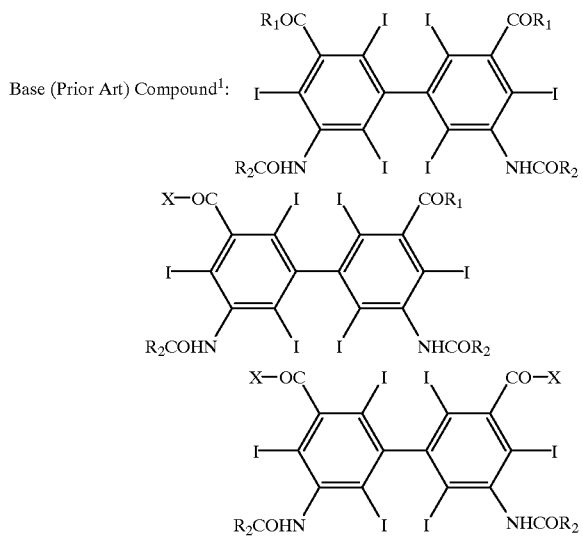

Where X is as defined above

| R$_1$ | R$_2$ |
|---|---|
| 1 N(CH$_2$CH$_2$OH)CH$_2$CH(OH)CH(OH)CH$_2$OH | CH(OH)CH$_2$OH |
| 2 N(CH$_2$CH$_2$OH)CH$_2$CH(OH)CH(OH)CH$_2$OH | CH(CH$_2$OH)$_2$ |
| 3 N(CH$_2$CH(OH)CH$_2$OH)CH$_2$CH(OH)CH(OH)CH$_2$OH | CH(OH)CH$_3$ |

[1]Petta et al., Nonionic Compact Dimers. Acad Radiol. 5, 41–48 (1998)

The foregoing compounds are made in accordance with the procedures described herein, or variations thereof that will be apparent to those skilled in the art in light of the specific compound desired.

To form salts of the foregoing compounds, any of the conventional physiologically acceptable counterions are suitable. In general, salts of the active compound may have the general formula $R^+X^-$, where $R^+$ is the active compound as described above and $X^-$ is $Cl^-$, $HCOO^-$, $H_2citrate^-$, $CH_3COO^-$, $NH_2CH_2COO^-$, $HCO_3^-$, $H_2PO_4^-$, or $HSO_3^-$.

As noted above, the new compounds of this invention are useful as contrast media, and are especially suited for use in urography, angiography, bronchography, etc., for visualization of body cavities and also for computer tomography.

B. Formulations and Administration.

The preparation and administration of new contrast media from the compounds of this invention is in accordance with known techniques. For example, the contrast compound can be combined with conventional galenic adjuvants to form a composition suitable for the desired method of application.

For example, the compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For enteral application, particularly suitable are tablets or dragees having the talc and/or a carbohydrate carrier or binder or the like, the carrier preferably being lactose and/or corn starch and/or potato starch. A syrup or the like can be used wherein a sweetened vehicle is employed. Sustained release compositions can also be formulated wherein the active compound is protected with differentially degradable coatings, e.g., by microencapsulation, multiple coatings, etc.

The concentration of the new contrast media of this invention in aqueous media depends on the particular diagnostic method involved. The preferred concentrations and doses of the compounds of this invention, e.g., for X-ray diagnoses, are concentrations of 50–400 mg of iodine per ml and doses of 10–500 ml. Concentrations of 100–350 mg of iodine per ml are especially preferred.

The precise method and details of application depend on the organ which is to be visualized and can be determined by fully conventional considerations, e.g., in analogy with conventional media such as those described in U.S. Pat. No. 4,264,572.

In the Examples below, DMAP means dimethylaminopyridine, DMAc means dimethylacetamide, BOC means t-butylcarbamate; DMF means dimethylformamide; nMM means N-methylmorpholine; nMP means N-methylpiperidine; 4MP means 4-methylpiperidine; iBCF means isobutylchloroformate; DIEA means diethylamine; THF means tetrahydrofuran; Fmoc means 9-fluorenylmethoxycarbonyl; Lys means lysine; AcOH means acetic acid AcOEt means ethyl acetate, NMR means Nuclear Magnetic Resonance Spectroscopy, TLC means thin layer chromatography; N means Normal, h means hour, min. means minutes, RT means room temperature, and temperatures are given in degrees centigrade.

EXAMPLE 1

Preparation of Lvs(Boc)4MP

This example describes the preparation of the intermediate Lys(Boc)4MP. The reaction schemes are outlined below.

In reaction 1, step 1, a solution of FmocLys(Boc) (1 Equiv) and nMM (1 Equiv) in THF is cooled to 0° C. and iBCF (1 Equiv) is added. In step 2, after 15 minutes 4-methylpiperidine (1 Equiv) is added and the mixture is maintained at 0° C. for 10 minutes and then allowed to warm to room temperature for 40 minutes. In step 3, the reaction mixture is concentrated under reduced pressure and extracted with EtOAc; washed (0.5 N KHCO$_3$, 0.5 N HCl) and evaporated. TLC is performed to verify reaction components.

In reaction 2, step 1, the crude FmocLys(Boc)4MP is dissolved in THF and DIEA (9/1, v/v) and allowed to stand at RT for 2 h. In step 2, the reaction mixture is concentrated under reduced pressure and triturated with ether/hexane (4/1, v/v). TLC is performed as well as NMR and Mass Spectrometry.

FmocLys(Boc)-Co$_2$H

RXN 1 STEP 1 | nMM, iBCF, THF
0° C.
5 min.

-continued

FmocLys(Boc)-CO$_2$CO$_2$CH$_2$CH(CH$_3$)

STEP 2 | 4MP
0° C. for 10 min.
warm to RT for 2h

STEP 3 | concentrate
extract

-continued

FmocLys(Boc)4MP, crude

RXN 2 STEP 1 | solvent (THF or DMF)
DIEA
RT for 2h

STEP 2 | concentrate
triturate with ether
/hexane 4/1 v/v

Lys(Boc)4MP

EXAMPLES 2–5
Preparation of Compound 1

Examples 2–5 illustrate the preparation of Compound 1 above, which is illustrative of Formula I above.

EXAMPLE 2
Acetate Protection of the Hydroxyl Group

The compound N-(2-hydroxyethyl)-2,4,6-triiodo-5-[2-(2, 4,6-triiodo-3-(N-methylacetamido)-5-(methylcarbamyl) benzamido acetamido]-isophthalmic acid, ioxaglate (CAS 59017-64-0) is placed into a 3-necked round bottom flask equipped with a mechanical stirrer and dropping funnel. A catalytic amount of DMAP is added. DMAc is then added to the flask. Next, acetic anhydride (1.6 Equiv) is added dropwise and the mixture stirred at room temperature overnight. Finally, water is added and the mixture filtered, collecting the product. The solid product is dried in a vacuum oven at 70° C. for 3 days prior to use.

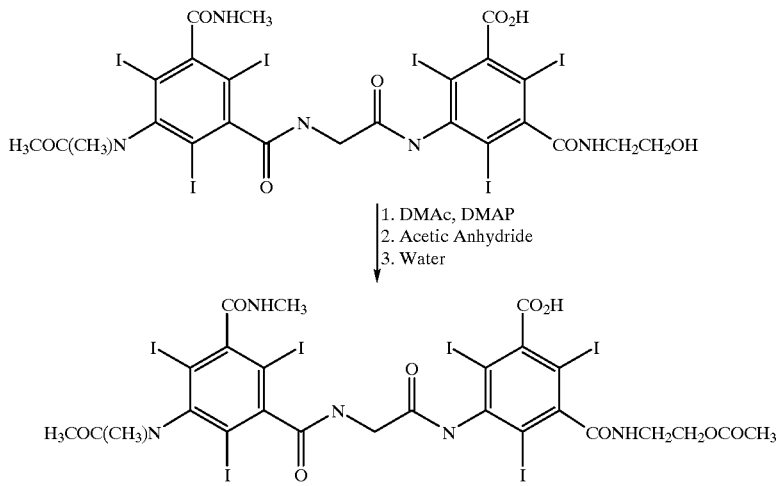

EXAMPLE 3
Acid Chloride Formation

In step 1, the product of Example 2 is placed in a 3-necked round bottom flask equipped with a mechanical stirrer, a dropping funnel and a condenser.

In step 2, thionyl chloride (16 Equiv.) is rapidly added to the flask via the dropping funnel. The solution is heated to 80–85° C. with an oil bath for three hours.

In step 3, check for product by thin layer chromatography (100% ethyl acetate).

In step 4, the condenser is replaced with a distilling arm. Excess thionyl chloride is removed by distillation under house vacuum (oil bath temperature 50° C.).

In step 5, THF is added and distilled. The addition/distillation is repeated twice.

In step 6, the product (AcHexCl) is extracted as an oil with ethyl acetate, washing with saturated NaHCO₃ and NaCl. The product is dried over Na₂SO₄, filtered and concentrated under reduced pressure.

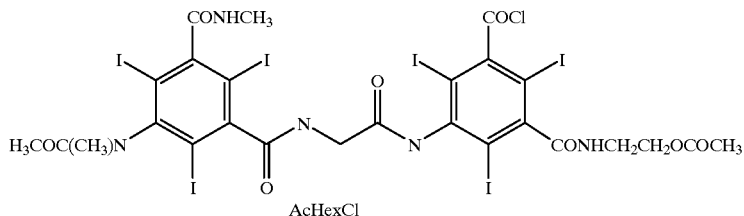

AcHexCl

EXAMPLE 4

Amide Coupling Reaction

In step 1, the product of Example 3 (AcHexCl) and sodium carbonate (1 Equiv) is placed in a round bottom flask equipped with a magnetic stir bar. Anhydrous DMAc is added and stirred under nitrogen for five minutes.

In step 2, the product of Example 1 is added (41% w/v in DMAc, 1.5 Equiv.) via a syringe to the flask. The contents are stirred overnight under nitrogen at room temperature.

In step 3, the reaction mixture is filtered through celite and the DMAc is removed by distillation under high vacuum.

In step 4, methanol is added to dissolve the oil and then water is added. The reaction solution is passed through an IRA-120H resin and the eluent collected. The resin is washed with water/methanol (1:1, v/v) and the eluent washes combined. The solution is then used for the acidic deprotection of the compound.

The product of Example 4 is acidified to pH 1.0 in methanol/water solution with concentrated H₂SO₄.

The mixture is then heated with an oil bath to reflux for 2 hours and the product concentrated.

Water is then added and the mixture is heated to reflux for an additional two hours, and the product is concentrated.

Water is then added and the mixture heated to reflux with a Dean Stark trap. The distillate is collected in the trap and allowed to cool to room temperature overnight.

The solution is subjected to TLC with EtOAc/Methanol/AcOH, 10:5:1 v/v/v.

The filtrate is then placed on an exchange column (Amberlite IRA-68 weakly basic anion exchange resin on top of IRA-458 strongly basic anion exchange resin) and the filtrate collected and the column washed with deionized water.

The filtrate is concentrated under reduced pressure and then under high vacuum with the flask warmed at 50° C. in a water bath overnight.

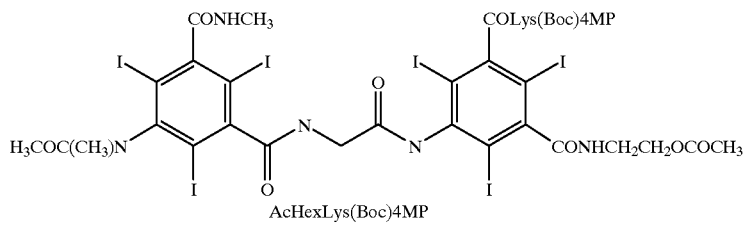

AcHexLys(Boc)4MP

EXAMPLE 5

Acidic Deprotection

The product of Example 4 is deprotected to yield Compound 1 illustrated below as follows.

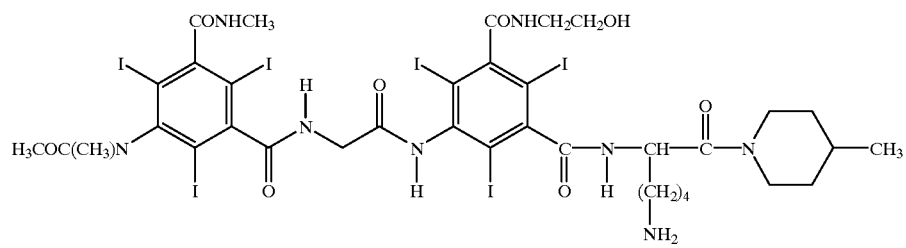

Compound 1

EXAMPLES 6–8

Preparation of Compound 10

These examples describe the preparation of Compound 10, which is illustrative of Formula II above.

EXAMPLE 6

Acid Chloride Formation

Thionyl chloride (16 Equiv.) is added dropwise to a solution of iothalamic acid (CAS 2276-90-6). The solution is heated and stirred for 3 hours. After removal of excess thionyl chloride by distillation, the product is extracted and concentrated under reduced pressure.

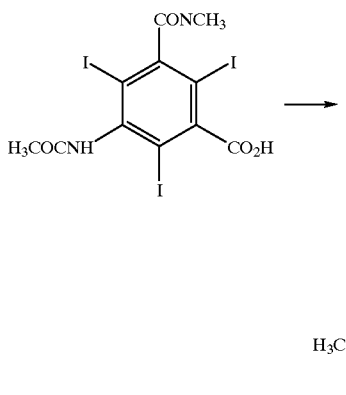

EXAMPLE 7

Amide Coupling

Lys(Boc)4MP prepared as described in Example 1 (1.5 Equiv.) is added to a sodium carbonate solution of the acid chloride under nitrogen and stirred overnight at room temperature. The reaction mixture is filtered, concentrated, and extracted to yield the protected amide intermediate illustrated below.

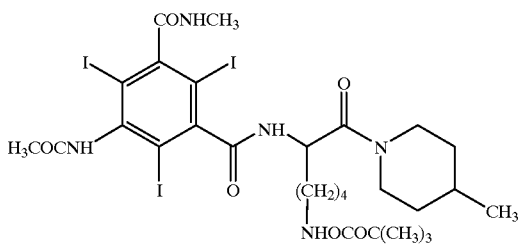

EXAMPLE 8

Acidic Deprotection

The intermediate prepared in example 7 is dissolved in trifluoroacetic acid and dichloromethane (1:1 v/v) and allowed to stand at room temperature for 1 hour. The reaction mixture is concentrated under reduced pressure and the product is crystallized to yield Compound 10 shown below.

Compound 10

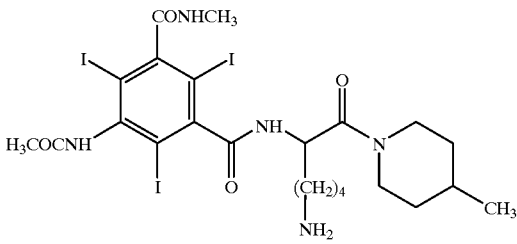

EXAMPLE 9

Formulations and Administration of Active Compound

Compound 1 and Compound 10 as described above are prepared as a formulation as follows:

320 mg Iodine/ml (420 mM of compound 1 and 845 mM of compound 10) is pH adjusted to 7.4 to 8.8 with NaOH or HCl in an aqueous solution consisting of 10 mM tromethane (Tris), 0.10 mg/ml edetate calcium disodium, 19 mM NaCl, and 0.3 mM Calcium chloride, dihydrate. This formulation is used in the dose regimens described below.

Selective coronary arteriography with or without left ventriculography., The usual dose for left coronary is 2–14 mL (typically 8 mL) of the formulation described above, and the usual dose for right coronary arteriography is 1 to 10 mL (typically 5 mL) of the formulation described above. The doses may be repeated as necessary. Doses up to a total of 150 mL are suitable. For left ventriculography, the usual dose in a single injection is 35–45 mL (typically 45 mL) and repeated as necessary. The total dose for combined selective coronary arteriography and left ventriculography should not exceed 250 mL.

Peripheral arteriography. The usual single adult dose for aorto-iliac runoff studies is 20 to 80 mL (typically 45 mL). The usual single adult dose for the common iliac, the external iliac and the femoral arteries is 10–50 mL (typically 30 mL). These doses may be repeated as necessary. For the upper limb, the usual single adult dose is 20 mL (range 15–30 mL) repeated as necessary. The total procedural dose should not exceed 250 mL.

Aortography and selective visceral arteriography. The usual dose for injections into the aort is 25 to 50 mL; the usual dose for injection into the celiac artery is 40 mL; the usual dose for injection into the superior mesenteric artery is 20 to 40 mL; the usual dose for injection into the inferior mesenteric artery is 8 to 15 mL. These doses may be repeated as necessary. The total dose should not exceed 250 mL.

The foregoing is illustrative of the present invention, and is not to be construed as limiting thereof. The invention is defined by the following claims, with equivalents of the claims to be included therein.

We claim:
1. A compound of the formula:

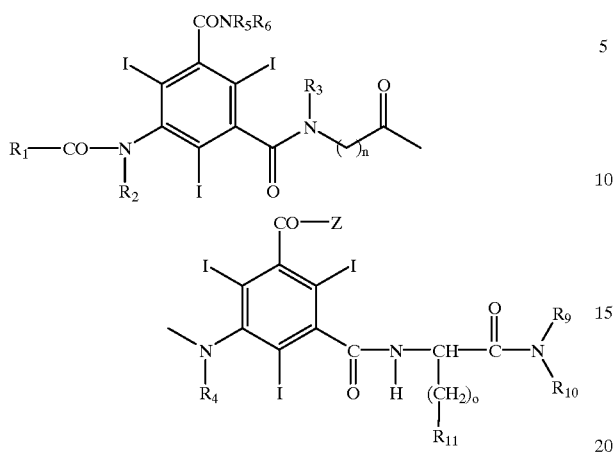

wherein:
R1 is selected from the group consisting of alkyl and alkyl substituted with hydroxy or alkoxy;
R2, R3 and R4 are each independently selected from the group consisting of hydrogen and alkyl;
R5 and R6 are each independently selected from the group consisting of hydrogen, alkyl and hydroxyalky,
n is from 1 to 3;
Z is —A—NHCH3 or Z is hydroxy-C2-5-alkylamino;
A is:

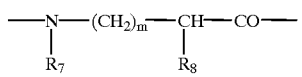

wherein
R7 is H or alkyl;
R8 is H, alkyl, or alkyl substituted by hydroxy or alkoxy; or together R7 and R8 form a propylene or hydroxypropylene ring;
m is 0 or 1;
R9 and R10 are each independently H or alkyl; or R9 and R10 together form C4–C8 alkylene which is unsubstituted or substituted from one to three times with alkyl or hydroxy;
R11 is amino or guanidino;
o is from two to six;
or a physiologically acceptable salt thereof.

2. A compound according to claim 1, wherein R3 and R4 are each hydrogen.
3. A compound according to claim 1, wherein $R_{12}$ is hydrogen and $R_5$ is alkyl.
4. A compound according to claim 1, wherein n is 1.
5. A compound according to claim 1, wherein R1 is alkyl.
6. A compound according to claim 1, wherein R2 is alkyl.
7. A compound according to claim 1, wherein Z is —NCH$_2$CH$_2$OH.
8. A compound according to claim 1, wherein o is 4.
9. A compound according to claim 1, wherein $R_{11}$ is amino.
10. A compound according to claim 1, wherein $R_9$ and $R_{10}$ together form C5 alkylene, which alkylene is unsubstituted or substituted once with alkyl.

11. A compound of the formula:

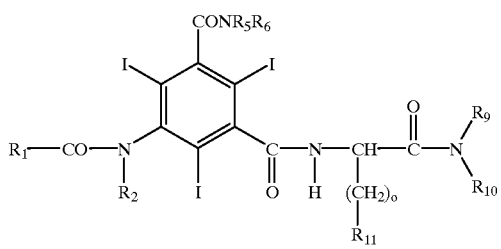

wherein:
R1 is selected from the group consisting of alkyl and alkyl substituted with hydroxy or alkoxy;
R2 is selected from the group consisting of hydrogen and alkyl;
R5 and R6 are each independently is selected from the group consisting of hydrogen, alkyl and hydroxyalky,
R9 and R10 are each independently H or alkyl; or R9 and R10 together form C4–C8 alkylene which is unsubstituted or substituted from one to three times with alkyl or hydroxy;
R11 is amino or guanidino;
o is from two to six;
or a physiologically acceptable salt thereof.

12. A compound according to claim 11, wherein $R_1$ is alkyl, which is unsubstituted or substituted with hydroxy.
13. A compound according to claim 11, wherein $R_2$ is hydrogen.
14. A compound according to claim 11, wherein $R_{12}$ is hydrogen and $R_5$ is alkyl.
15. A compound according to claim 11, wherein o is 4.
16. A compound according to claim 11, wherein $R_{11}$ is amino.
17. A compound according to claim 11, wherein $R_9$ and $R_{10}$ together form C5 alkylene, which alkylene is unsubstituted or substituted once with alkyl.
18. A contrast media comprising an amount of a compound according to claim 1 effective as a contrast medium in combination with a pharmaceutically acceptable carrier.
19. A method of visualizing an internal organ or structure of a patient, comprising the steps of:
administering to the patient an amount of a compound according to claim 1 effective as a contrast medium, and then
exposing said organ or structure to a diagnostic imaging treatment.
20. A contrast media comprising an amount of a compound according to claim 11 effective as a contrast medium in combination with a pharmaceutically acceptable carrier.
21. A method of visualizing an internal organ or structure of a patient, comprising the steps of:
administering to the patient an amount of a compound according to claim 11 effective as a contrast medium, and then
exposing said organ or structure to a diagnostic imaging treatment.

* * * * *

UNITED STATES PATENT AND TRADEMARK OFFICE
CERTIFICATE OF CORRECTION

PATENT NO. : 6,265,610 B1
DATED : July 24, 2001
INVENTOR(S) : Gabriel et al.

It is certified that error appears in the above-identified patent and that said Letters Patent is hereby corrected as shown below:

Column 8,
Between structures beginning at line 25 and line 35, insert the following:
-- where x = --

Column 17,
Line 28, should read as follows:
-- group consisting of hydrogen, alkyl and hydroxyalkyl, --

Line 53, should read as follows:
-- 3. A compound according to claim 1, wherein $R_6$ is --

Line 59, should read as follows:
-- —$NHCH_2CH_2OH$. --

Column 18,
Line 21, should read as follows:
-- group consisting of hydrogen, alkyl and hydroxyalkyl, --

Line 34, should read as follows:
-- 14. A compound according to claim 11, wherein $R_6$ is --

Signed and Sealed this

Eighteenth Day of March, 2003

JAMES E. ROGAN
*Director of the United States Patent and Trademark Office*